United States Patent [19]

Aldrich et al.

[11] 4,218,448
[45] Aug. 19, 1980

[54] ANTIHYPERTENSIVE POLYFLUOROHYDROXYISOPROPYL BICYCLIC AND TRICYCLIC CARBOSTYRILS

[75] Inventors: Paul E. Aldrich, Wilmington, Del.; Gilbert H. Berezin, West Chester, Pa.

[73] Assignee: E. I. Du Pont de Nemours and Company, Wilmington, Del.

[21] Appl. No.: 863,270

[22] Filed: Dec. 22, 1977

Related U.S. Application Data

[63] Continuation-in-part of Ser. No. 793,711, May 6, 1977, abandoned, which is a continuation-in-part of Ser. No. 699,587, Jun. 24, 1976, abandoned.

[51] Int. Cl.² .................. C07D 215/22; C07D 215/18; A61K 31/55; A61K 31/47
[52] U.S. Cl. ........................................ 424/244; 546/76; 546/98; 546/157; 260/244.4; 424/258
[58] Field of Search ........... 260/289 C, 287 P, 289 K, 260/239 BB, 244.4; 424/258; 546/157, 76, 98

[56] References Cited

U.S. PATENT DOCUMENTS

| | | | |
|---|---|---|---|
| 3,907,807 | 9/1975 | Meyer | 260/287 R |
| 4,058,612 | 11/1977 | Neustadt | 260/553 X |

FOREIGN PATENT DOCUMENTS 1394374  5/1975  United Kingdom ............... 260/289 C

*Primary Examiner*—Glennon H. Hollrah
*Assistant Examiner*—D. B. Springer

[57] ABSTRACT

Polyfluorohydroxyisopropyl bicyclic and tricyclic carbostyrils, such as 1,2-dihydro-8-[2,2,2-trifluoro-1-hydroxy-1-(trifluoromethyl)ethyl]-6-methyl-4H-pyrrolo-[3,2,1-ij]quinolin-7-one, useful as antihypertensive agents.

69 Claims, No Drawings

ANTIHYPERTENSIVE POLYFLUOROHYDROXYISOPROPYL BICYCLIC AND TRICYCLIC CARBOSTYRILS

CROSS REFERENCE TO RELATED APPLICATIONS

This application is a continuation-in-part of Ser. No. 793,711, filed May 6, 1977, now abandoned which in turn is a continuation-in-part of Ser. No. 699,587, filed June 24, 1976, now abandoned.

BACKGROUND

This invention relates to polyfluorohydroxyisopropyl bicyclic and tricyclic carbostyril antihypertensives.

Allied Chemical Corporation, in British Pat. No. 1,029,048, discloses hexahalohydroxyisopropyl aryl derivatives as intermediates in the preparation of aromatic carboxylic acids.

Jones, E. S, in U.S. Pat. Nos. 3,405,177 and 3,541,152, discloses hexahalohydroxyisopropyl aromatic amines useful as intermediates in the preparation of azo dyestuffs, polyesters, polyamides, insecticides, plasticizers, and pharmaceuticals.

Gilbert, E. E., in U.S. Pat. No. 3,532,753, discloses aromatic amino derivatives of hexahaloacetone useful as insecticides.

German OS No. 2,552,993 discloses compounds containing a ureido or isoureido function which have utility as antihypertensive agents.

Myer, H., et al., in U.S. Pat. No. 3,907,807, discloses benzoquinolizine antihypertensive agents; the following compound is exemplary:

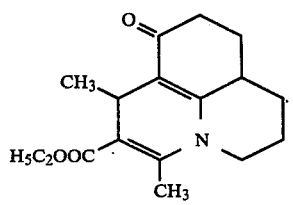

Many current antihypertensive agents produce unwanted side effects because of their undesirable mechanism of action. For example, guanethidine is an adrenergic neurone blocker, mecamylamine is a ganglion blocker, phenoxybenzamine is an α-adrenergic receptor blocker, and reserpine is a catecholamine depletor. Each of these mechanisms of action is undesirable because of the serious side effects produced. The compounds of this invention appear to lower blood pressure by a desirable mechanism of action - direct peripheral vasodilation - and, therefore have a distinct advantage over the above undesirable acting antihypertensive agents.

Furthermore, these compounds do not appear to produce central nervous system effects such as those seen with clonidine and α-methyldopa administration.

SUMMARY

According to this invention there is provided compounds of the following formula, processes for their manufacture, pharmaceutical compositions containing them, and methods of using them to treat hypertension in mammals.

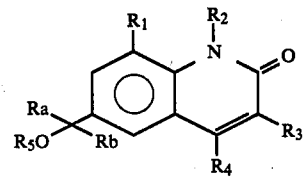

where
$R_1$ = H or alkyl of 1-4 carbons;
$R_2$ = H or alkyl of 1-4 carbons;
provided when $R_1$ = alkyl, $R_2$ = H, —$CH_3$ or —$CH_2CH_3$; or
$R_1+R_2$, taken together, can be:

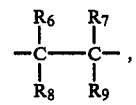 (a)

where
$R_6$ = H or —$CH_3$;
$R_7$ = H or —$CH_3$;
$R_8$ = H or alkyl of 1-4 carbons;
$R_9$ = H or alkyl of 1-4 carbons; or
$R_8+R_9$, taken together, can be —$(CH_2)_4$—;
provided
  (i) at least one of $R_6,R_7,R_8$, or $R_9$ = H; and
  (ii) the sum of the carbons of $R_6,R_7,R_8$, and $R_9$ is not more than 6;

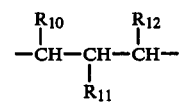 (b)

where
$R_{10}$ = H, —$CH_3$, or —$CH_2CH_3$;
$R_{11}$ = H, —$CH_3$, or —$CH_2CH_3$;
$R_{12}$ = H, —$CH_3$, or —$CH_2CH_3$; or
$R_{11}$, taken together with $R_{10}$ or $R_{12}$, can be —$(CH_2)_4$—;
provided at least one of $R_{10},R_{11}$, or $R_{12}$ = H; or
(c) —$(CH_2)_4$—;
$R_3$ = H, $CH_3$, F, Cl, Br, $NO_2$, $NH_2$, or OH;
$R_4$ = *H or alkyl or* 1-4 carbons;
$R_5$ = H, benzyl, acyl, or alkyl or 1-6 carbons;
$R_a$ = $CF_3$, $CF_2Cl$ or $CF_2H$;
$R_b$ = $CF_3$, $CF_2Cl$ or $CF_2H$; and
when $R_5$ = H, its pharmaceutically suitable metal salt.

Pharmaceutical Salts

Pharmaceutically suitable metal salts can be readily prepared from compounds where $R_5$ = H. Salts include those of metals such as sodium, potassium and calcium. The salts can be made in accordance with well-known techniques in the art. In use as antihypertensives, the salts are readily hydrolyzed to compounds where $R_5$ = H.

DETAILED DESCRIPTION

Preferred Compounds

Preferred for their high degree of activity are those compounds of Formula I where $R_1$ and $R_2$, taken together, are:

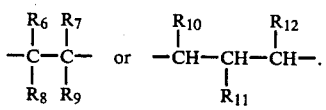

Also preferred are those compounds where, taken independently:
(a) $R_3$ is hydrogen; or
(b) $R_4$ is methyl or ethyl; or
(c) $R_5$ is hydrogen.

More preferred are those compounds where $R_1$ and $R_2$ taken together, are:

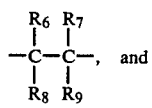

$R_6$, $R_7$, and $R_8$ are hydrogen or

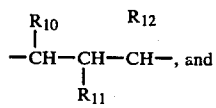

$R_{10}$ and $R_{11}$ are hydrogen.
Still more preferred are those compounds where:
(a) $R_1$ and $R_2$, taken together are:

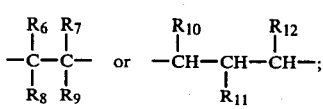

(b) $R_3$ is hydrogen;
(c) $R_4$ is methyl or ethyl;
(d) $R_6$, $R_7$ and $R_8$ are hydrogen or $R_{10}$ and $R_{11}$ are hydrogen;
(e) $R_5$ is as defined and more preferably is hydrogen; and
(f) Ra and Rb are as defined and more preferably Ra is $CF_3$ and Rb is $CF_3$, $CF_2Cl$ or $CF_2H$.

When $R_5$=alkyl, a preferred definition is alkyl of 1–4 carbons and more preferably 1–2 carbons.

The following compounds are specifically preferred:
2,3-dihydro-9-[2,2,2-trifluoro-1-hydroxy-1-(trifluoromethyl)ethyl]-7-methyl-1H,5H-benzo[ij]quinolizin-5-one; 2,3-dihydro-3,7-dimethyl-9-[2,2,2-trifluoro-1-hydroxy-1-(trifluoromethyl)ethyl]-1H,5H-benzo[ij]quinolizin-5-one; 2,3-dihydro-7-ethyl-9-[2,2,2-trifluoro-1-hydroxy-1-(trifluoromethyl)ethyl]-1H,5H-benzo[ij]quinolizin-5-one; 1,2-dihydro-8-[2,2,2-trifluoro-1-hydroxy-1-(trifluoromethyl)ethyl]-6-methyl-4-H-pyrrolo[3,2,1-ij]quinolin-4-one; 1,2-dihydro-2,6-dimethyl-8-[2,2,2-trifluoro-1-hydroxy-1-(trifluoromethyl)ethyl-4H-pyrrolo[3,2,1-ij]quinolin-4-one; 1,2-dihydro-6-ethyl-8-[2,2,2-trifluoro-1-hydroxy-1-(trifluoromethyl)ethyl]-4H-pyrrolo[3,2,1-ij]quinolin-4-one; 1,2-dihydro-8-[2,2-difluoro-1-hydroxy-1-(trifluoromethyl)ethyl]-6-methyl-4-H-pyrrolo[3,2,1-ij]quinoline-4-one; 1,2-dihydro-8-[2-chloro-2,2-difluoro-1-hydroxy-1-(trifluoromethyl)ethyl]-6-methyl-4H-pyrrolo[3,2,1-ij]quinoline-4-one; and 1,2-dihydro-8-[2,2-difluoro-1-hydroxy-1-(difluoromethyl)ethyl]-6-methyl-4H-pyrrolo[3,2,1-ij]quinolin-4-one.

Acyl Derivatives

Acyl derivatives of the hydroxy function of the compounds of this invention show excellent antihypertensive activity. The acyl derivatives (i.e., where $R_5$ is not hydrogen or alkyl) are hydrolyzed easily to the parent hydroxy compound ($R_5$=H), and it is believed that their antihypertensive effect is due to a facile in vivo hydrolysis. Acylation can be used to give derivatives with a variety of different physical properties, but with little difference in biological properties from the parent hydroxy compound. It is concluded, therefore, that the range of acyl groups is practically unlimited and not critical for antihypertensive activity. Among the acyl groups that can be used are alkanoyl, alkenoyl, and aroyl.

Synthesis

Hexafluorohydroxyisopropyl amine precursors are prepared in the following manner:
When $R_1$ and $R_2$ are hydrogen or alkyl of 1–4 carbon atoms and Ra and Rb are both $CF_3$, the precursors are prepared as shown in the following reaction scheme:

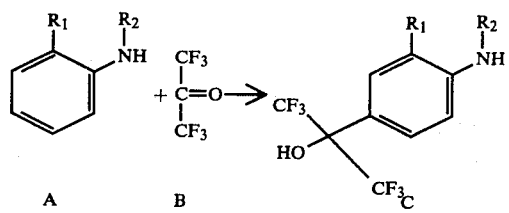

This reaction is described by Sheppard, W. A., J. Am. Chem. Soc., 87, 2410 (1965). A mixture of the appropriate aniline derivative, anhydrous aluminum chloride, and hexafluoroacetone is heated until the reaction is completed. The product is triturated with chloroform and cooled; then filtered off and recrystallized.

Precursors in which $R_1$ and $R_2$ are joined together and Ra and Rb are both $CF_3$ are prepared as shown in the following reaction scheme, which is more fully discussed in applicant's concurrently filed application Ser. No. 836,266, now U.S. Pat. No. 4,129,890, issued Dec. 12, 1978, which is a continuation-in-part of Ser. No. 793,712 filed May 6, 1977 now abandoned; which in turn is a continuation-in-part of Ser. No. 699,588, filed June 24, 1976, now abandoned, which claims these compounds.

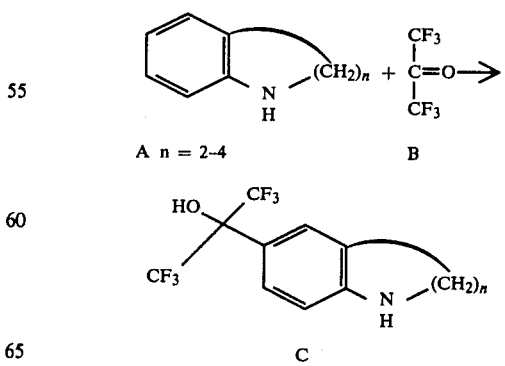

The reaction is conducted in a sealed pressure reactor at temperatures from 80°–200° C; it can also be conducted in a refluxing solvent, such as benzene or toluene, in a flask with hexafluoroacetone monohydrate, sesquihydrate, or trihydrate. Acidic catalysts such as AlCl₃, BF₃, or p-toluenesulfonic acid can be used but are not necessary. Reaction time is usually 4–12 hours. A temperature of 100°–120° C. and used of 1–5 mole percent of AlCl₃ are preferred.

A modified method for preparing these precursors (and those in which Ra and Rb are as defined) which produces higher yields for many of the compounds, especially the indolines, involves attaching a suitable protective group, such as benzyl, substituted benzyl, or benzhydryl at the basic nitrogen atom of the amine starting material, then contacting this protected compound with hexafluoroacetone, pentafluoroacetone, chloropentafluoroacetone, 1,1,3,3-tetrafluoroacetone, 1,3-dichlorotetrafluoroacetone, or 1-chloro-1,1,3,3-tetrafluoroacetone. The following diagram shows, in a general way, this reaction scheme illustrated by initial reaction of a benzyl halide followed by reaction of a protected compound with hexafluoroacetone.

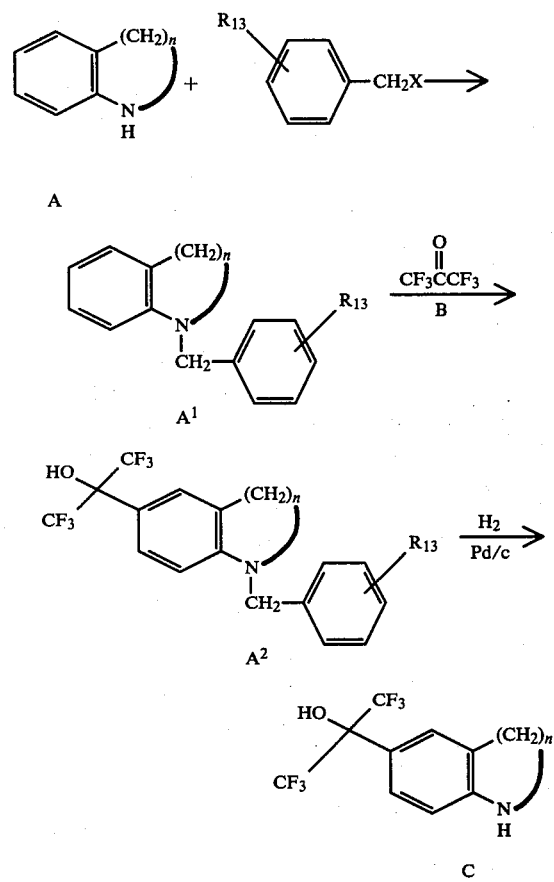

where
X=Cl or Br;
R₁₃=H, F, Cl, Br, NO₂, phenyl, or CH₃;
n=2, 3, or 4.

Starting amine (A) is treated with a benzyl halide to give a tertiary N-benzylamine (A¹). This is heated with hexafluoroacetone to give the adduct A², which is then hydrogenated to remove the benzyl group to give the desired compound (C). In a similar reaction procedure, the benzyl halide can be replaced by benzhydryl chloride or bromide in formation of a protected compound.

The protected compound (including adduct A¹ above) can be allowed to react with either hexafluoroacetone, pentafluoroacetone, chloropentafluoroacetone, or 1,1,3,3-tetrafluoroacetone, followed by hydrogenation. The benzhydryl protecting group is especially advantageous when 1,3-dichlorotetrafluoroacetone or 1-chloro-1,1,3,3-tetrafluoroacetone are used.

The hydrogenation step occasionally requires excess acid as a co-catalyst. Hydrogenolysis is attempted without addition of acid, and if little or no uptake of hydrogen is observed, acid is added (for example, concentrated hydrochloric acid), and the reaction is allowed to proceed.

The amine starting materials are either known in the art or easily prepared from those known in the art. Methods of making the various ring systems, however, are outlined as follows:

Indolines

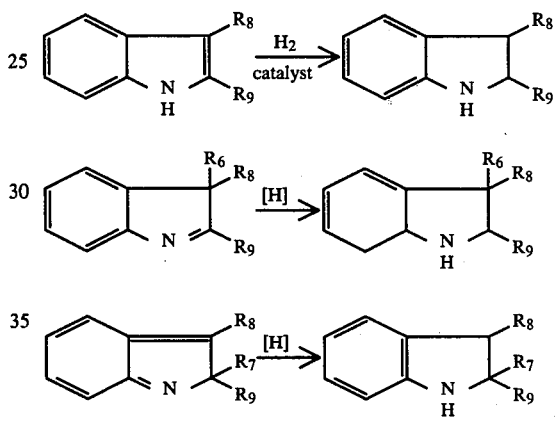

Tin and hydrochloric acid or zinc and hydrochloric acid can also be used as reducing agents.

See Elderfield, R. C., *Heterocyclic Compounds Vol.* 3, John Wiley & Sons, Inc., New York, N.Y. (1952) p.1.

Tetrahydroquinolines

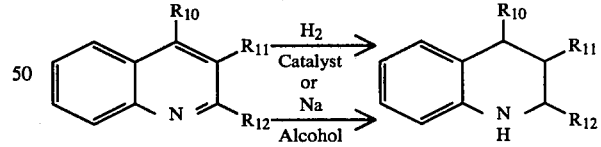

See Elderfield, R. C., *Heterocyclic Compounds* Vol. 4, John Wiley & Sons, Inc. New. York. N.Y. (1952) p.1.

Benzazepines

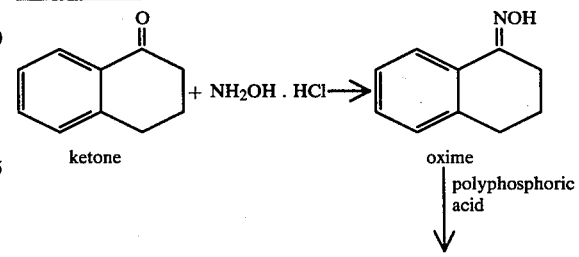

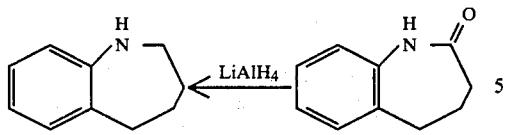

In the reaction scheme outlined 3,4-dihydro-1-(2H)-naphthalenone is contacted with hydroxylamine hydrochloride to give the corresponding oxime.

The oxime is rearranged by treatment with polyphosphoric acid to give the lactam 1,3,4,5-tetrahydro-1H-1-benzazepin-2-one.

Reduction of the lactam with LiAlH$_4$ gives 2,3,4,5-tetrahydro-1H-1-benzazepine.

The ketone starting materials for the parent systems discussed above are known in the art and are commercially available.

Intermediate amides (E) are prepared as shown in the following reaction:

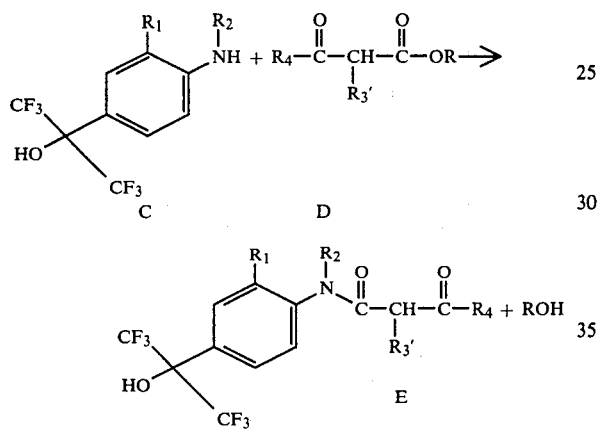

where R$_1$, R$_2$, and R$_4$ are as previously defined, R$'_3$ is hydrogen or CH$_3$, and R is an alkyl group of 1-5 carbons.

The amide (E) is prepared by heating equimolar amounts of amine (C) and 3-ketoester (D) in an oil bath. Th preferred temperature range is about 180°–220° C. Alternatively, the reactants can be refluxed together in a high-boiling solvent, for example, xylene.

The reaction can be conveniently followed by periodically removing a test portion and performing thin layer chromatography. When no further reaction is observed, the amide (E) is isolated by crystallization and/or chromatography. Occasionally, purification is difficult and, therefore, cyclization of the crude amide is more convenient.

When R$'_3$=H and R$_4$=CH$_3$ the amides (E) are prepared more conveniently and in better yield using diketene instead of the 3-ketoester (D). An equimolar amount of diketene is added to amine (C) dissolved in an inert solvent (for example, anhydrous tetrahydrofuran or toluene) held at 0° C. or room temperature. If the reaction is slow (as indicated by thin layer chromatography), the mixture is heated until no further reaction is observed. The crude product is often satisfactory for cyclization in sulfuric acid, but it can be purified by recrystallization and/or chromatography.

The final products are readily prepared as shown in the following cyclization reaction:

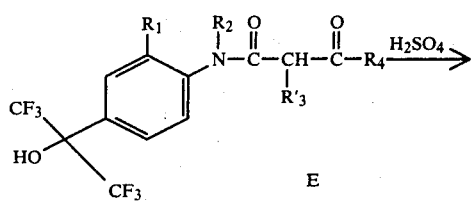

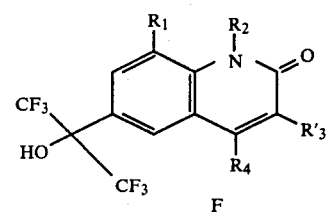

Cyclization is accomplished by heating the amide (E) in a condensing agent, such as sulfuric acid or polyphosphoric acid. Usually, heating in concentrated sulfuric acid on a steam bath for about 30–60 minutes completes the reaction, but occasionally higher heating (up to 120° C.) for a longer time (up to 24 hours) is necessary. Completion of the reaction can be conveniently checked by removing a small test sample, isolating the solids, and analyzing by thin layer chromatography. The product (F) is isolated by pouring the sulfuric acid solution into excess ice water, removing the precipitate by filtration, washing, and drying. Further purification, if necessary, can be done by recrystallization and/or chromatography.

When R$_1$ and R$_2$ are alkyl in FIG. E, cyclization is not observed. Compounds described by FIG. F where R$_1$ and R$_2$ are alkyl can be prepared by cyclization of the amide E where R$_1$ is alkyl and R$_2$ is H. The product F has R$_1$=alkyl and R$_2$=H. When the product F is treated with R$'_5$X, (R$'_5$=alkyl of 1–6 carbons or

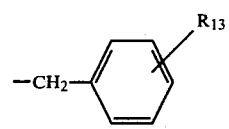

where R$_{13}$=H, F, Cl, Br, NO$_2$, phenyl, or CH$_3$; X=halogen), an alkyl halide such as methyl iodide or aralkyl halide such as benzylbromide, in a solvent such as dimethylformamide with a base such as potassium carbonate, or sodium hydride, the oxygen-alkylated compound F$_1$ is obtained.

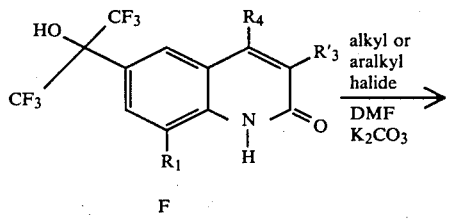

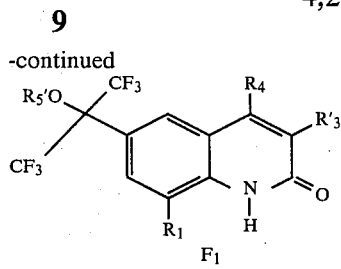

F₁

The compound F₁ may then be alkylated on nitrogen by use of base such as sodium hydride or thallium ethoxide in a solvent such as DMF with an alkyl halide or sulfate, R'₂X, (R'₂=—CH₃ or —CH₂CH₃, X=halogen or sulfate) to give F₂.

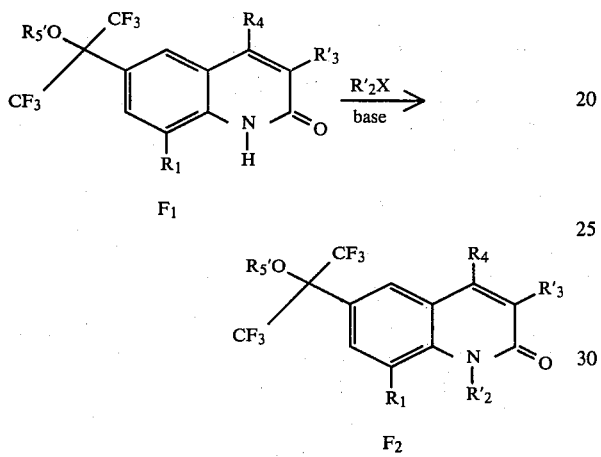

The alkyl or aralkyl group R'₅ on compound F₂ may be removed by an appropriate reaction such as hydrolysis with aqueous hydrobromic acid or hydrogenolysis to give compound F₃, where R₁ and R'₂ are alkyl.

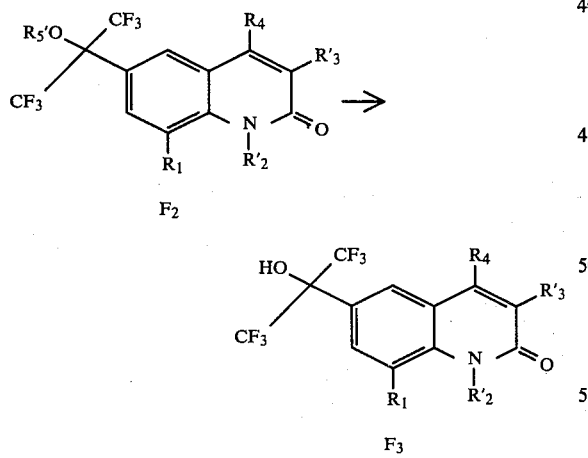

Compounds of formula I where R₃ is other than hydrogen or methyl are preferably prepared from F (R'₃=hydrogen) by well-known electrophilic substitution reactions, e.g., chlorination, bromination, and nitration. The NO₂ compound can be reduced to the NH₂ compound, which is in turn useful for preparing compounds where R₃=fluorine or OH.

To make compounds where R₄ is hydrogen the process is modified by using malonyl dichloride instead of ketoester (D). The resulting half-amide chloride of malonic acid (E, where R₄=Cl) is then cyclized with a suitable condensing agent, for example, phosphorous oxychloride, to give G, which can be hydrogenolytically cleaved to H.

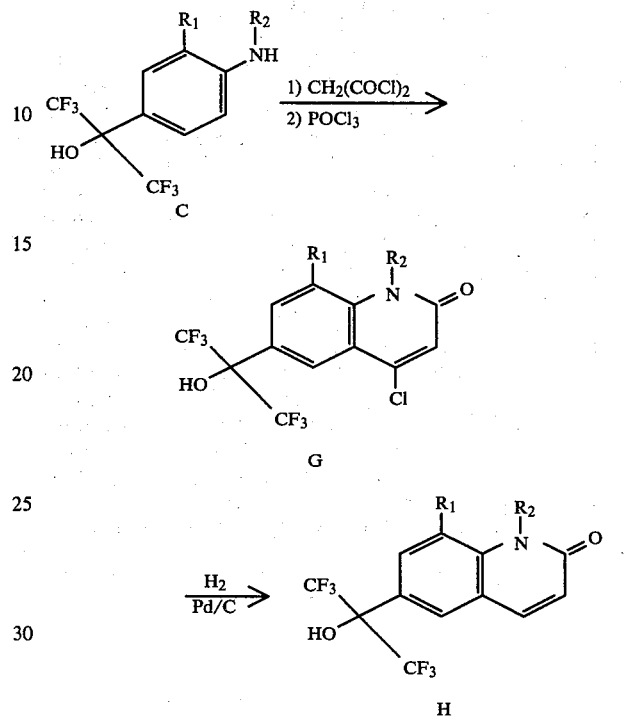

Alternatively, ethyl malonyl chloride can be used instead of ketoester (D) to give the half-amide ester of malonic acid (E, where R₄=OC₂H₅) which is cyclized with a condensing agent, for example, sulfuric acid, to give F where R₄ is OH. This is then treated with phosphorous pentachloride in phosphorous oxychloride solution to give G, which is converted to H as shown above.

Esters are prepared from F by reaction with acid chlorides or anhydrides with or without solvents. Because of the tertiary nature and high acidity of the alcohol group, esterification is rather slow at room temperature but can be greatly accelerated by using high boiling solvents (with or without the addition of a base) or using refluxing pyridine as a solvent and base.

Ethers are prepared from F by converting it to a salt by treating with a suitable base (for example, potassium tert-butoxide), then O-alkylating the salt by heating with a dialkyl sulfate or alkyl halide.

EXAMPLE 1

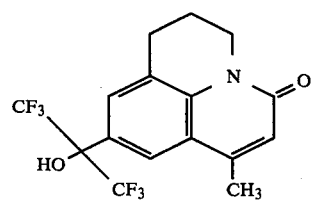

A. To a stirring solution of 32.9 g (0.11 mole) of α,α-bis(trifluoromethyl)-1,2,3,4-tetrahydro-6-quinoline-methanol in an inert solvent (e.g. dry toluene or tetrahydrofuran) is added 9.2 g (0.11 mole) of diketene. The mixture is refluxed for 30–40 minutes, cooled and evaporated. The residue is triturated with 150 ml of dibutyl ether to give crystals. The crystals are separated by filtration to give 24.8 g (64%) of α,α-bis(trifluoromethyl)-1-(1,3-dioxobutyl)-1,2,3,4-tetrahydro-6-quinolinemethanol, m.p. 115°–117°.

B. A stirred mixture of 6.0 g (0.02 mole) of α,α-bis(trifluoromethyl)-1,2,3,4-tetrahydro-6-quinolinemethanol, 2.6 g (0.02 mole) of ethyl acetoacetate, and 100 ml of xylene is refluxed for 16 hours. The mixture is allowed to cool and is evaporated. The residue is triturated with a mixture of toluene, ethyl acetate, and hexane (60:10:30). The insoluble portion is filtered off, washed with water, and dried to give 1.6 g (23%) of α,α-bis(trifluoromethyl)-1-(1,3-dioxobutyl)-1,2,3,4-tetrahydro-6-quinolinemethanol. C. A solution of 10.5 g (0.027 mole) of α,α-bis(trifluoromethyl)-1-(1,3-dioxobutyl)-1,2,3,4-tetrahydro-6-quinolinemethanol in 30 ml of concentrated sulfuric acid is heated on a steam bath for 30–45 minutes, cooled to approximately 60° C., and poured into ice. When the ice is melted, the precipitate is filtered off, washed with water, and dried. The solid is recrystallized from 2-ethoxyethanol to give 7.2 g (74%) of 2,3-dihydro-9-[2,2,2-trifluoro-1-hydroxy-1-(trifluoromethyl)ethyl]-7-methyl-1H,5H-benzo[ij]quinolizin-5-one, m.p. 295°–296°.

Anal. for $C_{16}H_{13}F_6NO_2$: Calc'd: C, 52.62; H, 3.59; N, 3.84. Found: C, 52.58; H, 3.78; N, 3.85.

EXAMPLE 2

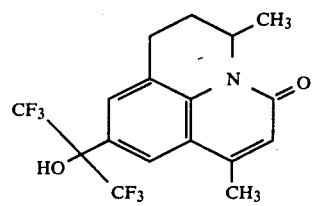

A stirred mixture of 23.5 g (0.075 mole) of α,α-bis(trifluoromethyl)-1,2,3,4-tetrahydro-2-methyl-6-quinolinemethanol, 100 ml of dry toluene, and 8.3 g (0.099 mole) of diketene is refluxed for 16 hours under dry nitrogen. The toluene is evaporated. The residue, which is crude α,α-bis(trifluoromethyl)-1-(1,3-dioxobutyl)-1,2,-3,4-tetrahydro-2-methyl-6-quinolinemethanol, is dissolved in 100 ml of concentrated sulfuric acid and is heated on a steam bath for one hour. The solution is poured into ice water. When the ice is melted, the insoluble material is extracted with ether. The ether solution is dried and evaporated to give 26.8 g of residue. Trituration of the residue with a mixture of toluene, hexane, and ethyl acetate (60:30:10) induces crystals to separate. The crystals are filtered off, and two recrystallizations from toluene and ethyl acetate mixture (9:1) gives 10.0 g (35%) of crystals of 2,3-dihydro-3,7-dimethyl-9-[2,2,2-trifluoro-1-hydroxy-1-(trifluoromethyl)ethyl]-1H,5H-benzo-[ij]quinolizin-5-one, m.p. 195°–198°.

EXAMPLES 3–7

The appropriate tetrahydroquinoline can be used in place of α,α-bis(trifluoromethyl)-1,2,3,4-tetrahydro-2-methyl-6-quinolinemethanol of Example 2 for conversion to the corresponding benzoquinolizinone as shown in the following chart:

| Example No. | Tetrahydroquinoline | Product |
|---|---|---|
| 3 | (structure) m.p. 158°–159° | (structure) m.p. 174°–177° |
| 4 | (structure) | (structure) |

| Example No. | Tetrahydroquinoline | Product |
|---|---|---|
| 5 | | |
| 6 | | |
| 7 | | |

EXAMPLE 8

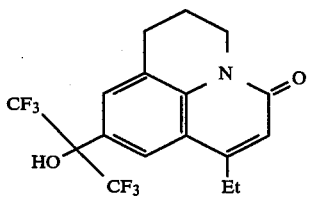

A mixture of 15.0 g (0.05 mole) of α,α-bis(trifluoromethyl)-1,2,3,4-tetrahydro-6-quinolinemethanol and 7.2 g (0.05 mole) of ethyl propionylacetate is heated with stirring in an open flask in an oil bath at 200°–220°. When the internal temperature rises to 180°–200°, the mixture is then allowed to cool. The crude product is chromatographed on silica gel successively with the following eluents: (1) toluene-hexane (60:40), (2) toluene-ethyl acetate-hexane (60:10:30), and (3) toluene-ethyl acetate-hexane (60:20:20). Later fractions yield 5.3 g (26%) of a red oil, which is identified by nmr spectroscopy as α,α-bis(trifluoromethyl)-1-(1,3-dioxopentyl)-1,2,3,4-tetrahydro-6-quinolinemethanol. The 5.3 g of oil is dissolved in 50 ml of concentrated sulfuric acid and heated on a steam bath for 45 minutes. The solution is poured into 300 ml of ice water. The precipitate is filtered off, washed with water, and dried. Chromatography on silica gel with toluene-ethyl acetate (60:40), followed by recrystallization from dibutyl ether, gives 0.7 g (14%) of 2,3-dihydro-7-ethyl-9-[2,2,2-trifluoro-1-hydroxy-1-(trifluoromethyl)-ethyl]-1H,5H-benzo[ij]-quinolizin-5-one, m.p. 209°–210°.

EXAMPLE 9

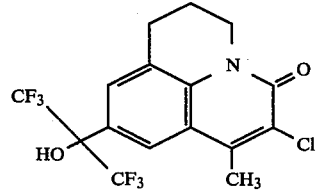

To a stirred suspension of 7.3 g (0.02 mole) of 6,7-dihydro-9-[2,2,2-trifluoro-1-hydroxy-1-(1-trifluoromethyl)ethyl]-1-methyl-3H,5H-benzo[ij]quinolizin-3-one in 100 ml of concentrated hydrochloric acid is gradually added 1.95 g (0.01 mole) of calcium hypochlorite (73.2%) by means of a powder addition funnel. The mixture is stirred for 5 hours at room temperature. The mixing is poured into 400 ml of cold water. The white solid is filtered off, washed with water, and dried to give 6.0 g of solid. A portion is purified by dissolving 4.2 g in 25 ml of trifluoroacetic acid and adding water, a little at a time, to incipient precipitation. The mixture is allowed to cool and crystallize to give 1.1 g of 6-chloro-2,3-dihydro-9-[2,2,2-trifluoro-1-hydroxy-1-(trifluoromethyl)ethyl]-7-methyl-1H,5H-benzo[ij]quinolizin-5-one, m.p. 266°–268°.

EXAMPLE 10

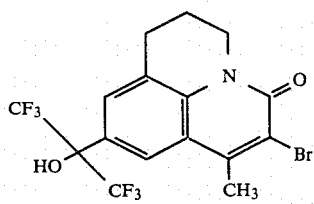

To a stirred suspension of 7.3 g (0.02 mole) of 6,7-dihydro-9-[2,2,2-trifluoro-1-hydroxy-1-(trifluoromethyl)ethyl]-1-methyl-3H,5H-benzo[ij]quinolizin-3-one in 100 ml of warm concentrated hydrochloric acid is added dropwise 3.2 g (0.02 mole) of bromine. The mixture is allowed to stir for 16 hours, and then the precipitate is filtered off, washed with water, and dried. The solid is recrystallized from alcohol and dried in an oven at 400° to give 6.3 g (71%) of white crystalline 6-bromo-2,3-dihydro-9-[2,2,2-trifluoro-1-hydroxy-1(trifluoromethyl)ethyl]-7-methyl-1H,5H-benzo-[ij]quinolizin-3-one, m.p. 265°-266°.

EXAMPLE 11

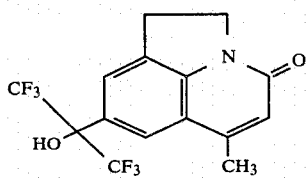

To a stirred solution of 343 g (1.25 mole) of α,α-bis(-trifluoromethyl)-2,3-dihydro-1H-indole-5-methanol in 1880 ml of dry tetrahydrofuran cooled in an ice bath is added dropwise 106 g (1.26 mole) of diketene. The solution is allowed to warm to room temperature for 16 hours and then is refluxed for 30 minutes. The solvent is evaporated to give 463 g (100%) of crude α,α-bis(trifluoromethyl)-1-(1,3-dioxobutyl)-2,3-dihydro-1H-indole-5-methanol, m.p. 150°-151°.

The product is added with stirring to 1450 ml of concentrated sulfuric acid, and the solution is heated on a steam bath for 45 minutes. The mixture is cooled to approximately 60° and is poured into ice water. The solid is filtered off, washed with water, and dried to give 315 g of crude solid. The solid is recrystallized from dimethylformamide to give 273 g (62%) of 1,2-dihydro-8-[2,2,2-trifluoro-1-hydroxy-1-(trifluoromethyl)ethyl]-6-methyl-4H-pyrrolo[3,2,1-ij]quinolin-4-one, m.p. 337°-338°.

EXAMPLE 12

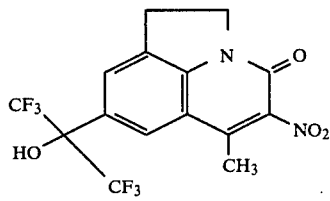

To a stirred mixture of 7.0 g (0.02 mole) of 1,2-dihydro-8-[2,2,2-trifluoro-1-hydroxy-1-(trifluoromethyl)-ethyl]-6-methyl-4H-pyrrolo[3,2,1-ij]quinolin-4-one and 70 ml of trifluoroacetic acid is added 4.2 g (0.042 mole) of potassium nitrate. The mixture is stirred for 16 hours at room temperature and then is refluxed for 30 minutes. The mixture is poured into 300 ml of water. The solid is filtered off, washed with water, and dried. Recrystallization from 250 ml of acetonitrile gives 3.3 g (42%) of 1,2-dihydro-8-[2,2,2-trifluoro-1-hydroxy-1-(trifluoromethyl)-ethyl]-6-methyl-5-nitro-4H-pyrrolo[3,2,1-ij]quinolin-4-one, m.p. 289°-290° (dec).

Anal. for $C_{15}H_{10}F_6N_2O_4$: Calc'd: C, 45.46; H, 2.54; N, 7.07. Found: C, 45.64; H, 2.79; N, 6.82

EXAMPLE 13

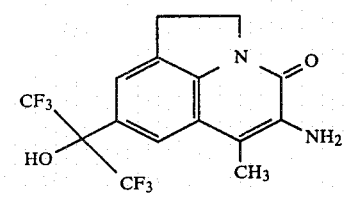

A mixture of 3.0 g. (0.0075 mole) of 1,2-dihydro-8-[2,2,2-trifluoro-1-hydroxy-1-(trifluoromethyl)ethyl]-6-methyl-5-nitro-4H-pyrrolo[3,2,1-ij]quinolin-4-one, 150 ml. of alcohol, and 0.5 g. of 10% palladium on charcoal is hydrogenated at an initial pressure of 3 atmospheres in a Parr shaker apparatus until uptake is complete. The catalyst is filtered off, and the filtrate is evaporated. Recrystallization of the residue from alcohol gives 1.7 g (62% ) of 1,2-dihydro-8-[2,2,2-trifluoro-1-hydroxy-1-(trifluoromethyl)-ethyl]-5-amino-6-methyl-4H-pyrrolo[3,2,1-ij]quinolin-4-one, m.p. 292°-293°.

EXAMPLE 14

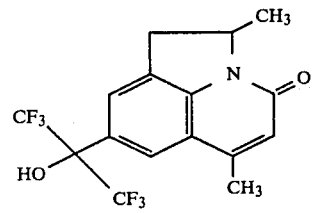

(a) To a stirred solution of 6.0 g (0.02 mole) of α,α-bis(trifluoromethyl)-2,3-dihydro-2-methyl-1H-indole-5-methanol in 50 ml of anhydrous tetrahydrofuran is added 1.9 g (0.022 mole) of diketene. After 16 hours at room temperature, the solution is refluxed for one hour. The solvent is evaporated, and the residue is recrystallized from dibutyl ether to give 5.7 g (74%) of α,α-bis(-trifluoromethyl)-1-(1,3-dioxobutyl)-2,3-dihydro-2-methyl-1H-indole-5-methanol, m.p. 118°-119°.

(b) A solution of 2.8 g (0.0073 mole) of the product in 10 ml of concentrated sulfuric acid is heated on a steam bath for 45 minutes. The solution is poured into ice water, and the precipitate is filtered off, washed with water, and dried to give 1.8 g of solid. Recrystallization from dibutyl ether gives 1.4 g (52%) of crystalline 1,2-dihydro-2,6-dimethyl-8-[2,2,2-trifluoro-1-hydroxy-1-(trifluoromethyl)-ethyl]-4H-pyrrolo[3,2,1-ij]quinolin-4-one, m.p. 230°-231°.

EXAMPLES 15–20

The appropriate indoline used in place of α,α-bis(trifluoromethyl)-2,3-dihydro-2-methyl-1H-indole-5-methanol of Example 14 can be converted to the corresponding heterocyclic ring-substituted derivative as shown in the following chart:

| Example No. | Indoline | Product |
|---|---|---|
| 15 | (structure) m.p. 163°–164° | (structure) m.p. 282°–283° |
| 16 | (structure) m.p. 89°–90° | (structure) m.p. 164°–165° |
| 17 | (structure) | (structure) |
| 18 | (structure) | (structure) |
| 19 | (structure) | (structure) |
| 20 | (structure) | (structure) |
| 21 | (structure) m.p. 120°–121° | (structure) m.p. 179°–181° |

EXAMPLE 22

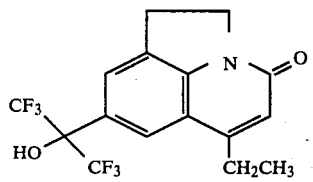

A. A stirred mixture of 13.7 g (0.05 mole) of α,α-bis(-trifluoromethyl)-2,3-dihydro-1H-indole-5-methanol and 7.2 g (0.05 mole) of ethyl propionylacetate is heated at 200° in an oil bath for 3 hours. The mixture is allowed to cool and is triturated with ether. The mixture is filtered, and the filtrate is evaporated. The residue is chromatographed on silica gel with a mixture of toluene-ethyl acetate (60:40). A fraction is obtained, which can be recrystallized from 1-chlorobutane to give 3.0 g (16%) of crystals, m.p. 118°-119°, α,α-bis(trifluoromethyl)-1-(1,3-dioxopentyl)-2,3-dihydro-1H-indole-5-methanol.

B. A stirred mixture of 2.9 g of α,α-bis(trifluoromethyl)-1-(1,3-dioxopentyl)-2,3-dihydro-1H-indole-5-methanol and 10 ml of concentrated sulfuric acid is heated on a steam bath for 45 minutes. The solution is poured into 100 ml of ice water. The precipitate is filtered off, washed with water, and dried. Recrystallization from dibutyl ether gives 0.6 g (22%) of 1,2-dihydro-6-ethyl-8-[2,2,2-trifluoro-1-hydroxy-1-(trifluoromethyl)ethyl]-4H-pyrrolo[3,2,1-ij]quinolin-4-one, m.p. 251°-252°.

EXAMPLE 22a

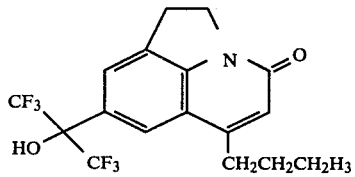

Use of ethyl valerylacetate in place of ethyl propionylacetate of Example 22 gives 1,2-dihydro-6-n-butyl-8-[2,2,2-trifluoro-1-hydroxy-1-(trifluoromethyl)ethyl]-4H-pyrrolo-[3,2,1-ij]quinolin-4-one.

EXAMPLE 23

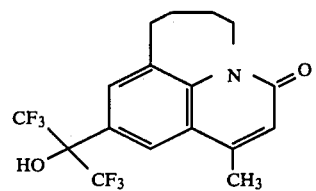

By the method shown in Example 14, α,α-bis(trifluoromethyl)-2,3,4,5-tetrahydro-1H-1-benzazepine-7-methanol is converted to α,α-bis(trifluoromethyl)-1-(1,3-dioxobutyl)-2,3,4,5-tetrahydro-1H-1-benzazepine-7-methanol, m.p. 169°-171°, which is cyclized by heating in sulfuric acid (in this instance at 120° for 24 hours) to give 5,6,7,8-tetrahydro-10-[2,2,2-trifluoro-1-hydroxy-1-(trifluoromethyl)ethyl]-1-methyl-3H-azepino[3,2,1-ij]quinolin-3-one, m.p. 197°-198°.

EXAMPLE 24

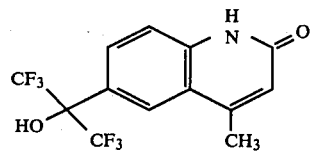

A mixture of 63.2 g (0.68 mole) of aniline, 2 g. of anhydrous aluminum chloride, and 135 g. (0.81 mole) of hexafluoroacetone is heated at 140° in an autoclave for 16 hours. The product is triturated with 800 ml of chloroform and cooled to 0°. The solid is filtered off and recrystallized from methylcyclohexane-dibutyl ether (50:50) to give 104 g (59%) of α,α-bis(trifluoromethyl)-4-aminobenzenecarbinol, m.p. 145°-150° [W. A. Sheppard, J. Am. Chem. Soc. 87, 2410 (1965), reports m.p. 150°-151.5°].

By the method shown in Example 14, the α,α-(trifluoromethyl)-4-amino-benzenecarbinol is converted to α,α-bis(trifluoromethyl)-4-(1,3-dioxobutylamino)benzenecarbinol, which is cyclized by heating in sulfuric acid to give 6-(2,2,2-trifluoro-1-hydroxy-1-(trifluoromethyl)ethyl)-4-methyl-2(1H)-quinolinone, m.p. 157°-158°.

EXAMPLES 25-30

By the procedure of Example 14b, the following compounds can be made from the appropriate starting materials, which are shown.

| Starting Materials | Products |
|---|---|
| 25 ![structure with CH3, CF3, HO, NH-C(=O)-CH2-C(=O)-CH3] | ![product structure with CH3, CF3, HO, N-H, =O, CH3] m.p. 282°-284° |

-continued

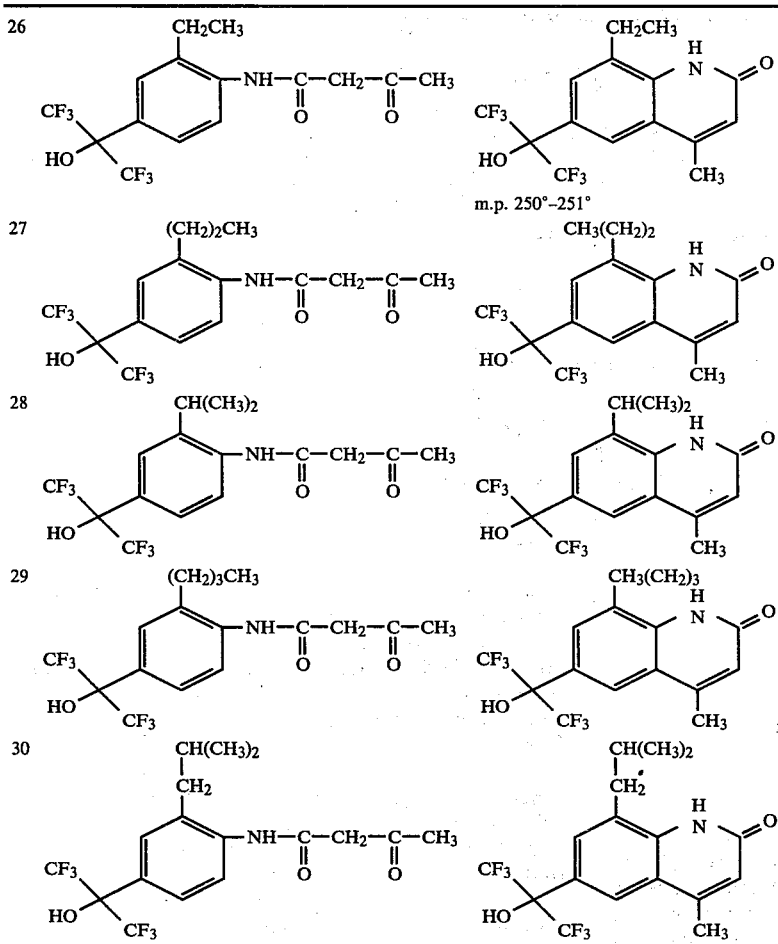

m.p. 250°–251°

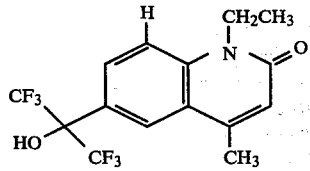

Example 31

A mixture of 82.0 g. (0.68 mole) of N-ethylaniline, 2 g. of anhydrous aluminum chloride, and 135 g. of hexafluoroacetone is heated at 140° in an autoclave for 16 hours. The crude product is chromatographed on 700 g. of silica gel with chloroform as eluent. The initial fractions are recrystallized from methylcylohexane to give 73 g. (37%) of α,α-bis(trifluoromethyl)-4-(ethylamino)-benzenecarbinol, m.p. 90°–92°

By the method shown in Example 14, the α,α-bis-(trifluoromethyl)-4-(ethylamino)-benzenecarbinol is converted to α,α-bis(trifluoromethyl)-4-[N-(1,3-dioxobutyl)-N-ethylamino]benzenecarbinol, m.p. 91°–92°, which is cyclized by heating in sulfuric acid to give 1-ethyl-6-[2,2,2-trifluoro-1-hydroxy-1-(trifluoromethyl-)ethyl]-4-methyl-2(1H)-quinolinone, m.p. 185°–187° (in this instance purified by trituration of the product with ether).

By the procedure of Example 14b, the following compounds can be made from the appropriate starting materials which are shown.

| Starting Materials | Products |
|---|---|
| 33. ![structure with CH2CH2CH3, N-C-CH2-C-CH3, CF3/HO/CF3 on phenyl] | ![quinolinone product with CH2CH2CH3, CF3/HO/CF3, CH3] |
| 34. ![structure with (CH2)3CH3, N-C-CH2-C-CH3, CF3/HO/CF3 on phenyl] | ![quinolinone product with (CH2)3CH3, CF3/HO/CF3, CH3] m.p. 138°–139.5° |
| 35. ![structure with CH2CH(CH3)2, N-C-CH2-C-CH3, CF3/HO/CF3 on phenyl] | ![quinolinone product with CH2CH(CH3)2, CF3/HO/CF3, CH3] |

EXAMPLE 36

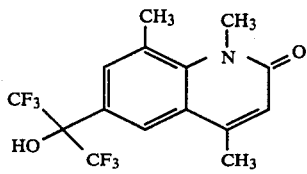

To a solution of 6-[2,2,2-trifluoro-1-hydroxy-1-(trifluoromethyl)ethyl]-4,8-dimethyl-2(1H)-quinolinone in dimethylformamide is added potassium carbonate and benzyl bromide. The solution is heated with stirring at reflux under nitrogen.

When the reaction is complete as indicated by thin layer chromatography, the solvent is removed at reduced pressure and the residual material is treated with water and extracted into ether. The ethereal solution is dried with anhydrous magnesium sulfate and filtered. The ether is evaporated at reduced pressure. The residual material is chromatographed on silicic acid to give 6-[2-2,2-trifluoro-1-benzyloxy-1-(trifluoromethyl)ethyl]-4,8-dimethyl-2(1H)-quinolinone, m.p. 162°–164°.

To a solution of 6-[2,2,2-trifluoro-1-benzyloxy-1-(trifluoromethyl)ethyl]-4,8-dimethyl-2(1H)-quinolinone in dimethylformamide is added an equivalent of thallium ethoxide. The solution is stirred under nitrogen. To the solution is added methyl iodide, and the solution is stirred and heated to 50° until thin layer chromatography indicates the reaction is complete. The solution is cooled and treated with 5 ml of methanol. The cooled solution is filtered and evaporated at reduced pressure. The residual material is extracted with hexane and the filtered solution is evaporated at reduced pressure. The residual material is heated to 250° in a nitrogen atmosphere for 4 hours. At the end of this period, the residual material is chromatographed on silicic acid to give 6-[2,2,2-trifluoro-1-benzyloxy-1-(trifluoromethyl)ethyl]-1,4,8-trimethyl-2(1H)-quinolinone.

To a solution of 6-[2,2,2-trifluoro-1-benzyloxy-1-(trifluoromethyl)ethyl]-1,4,8-trimethyl-2(1H)-quinolinone in ethanol is added 10% palladium on carbon catalyst. The solution is arranged on a Parr hydrogenation apparatus and shaken with 50 pounds of hydrogen pressure.

Shaking is continued until no further hydrogen uptake is noted. The solution is filtered and evaporated to give 6-[2,2,2-trifluoro-1-hydroxy-1-(trifluoromethyl)ethyl]-1,4,8-trimethyl-2(1H)-quinolinone, m.p. 241°–243°.

EXAMPLES 37–41

By a procedure similar to Example 36, the following compounds can be made from the appropriate starting materials.

| Starting Materials | Products |
|---|---|
| 37. ![quinolinone with CH3, H-N, CF3/HO/CF3, CH3] | ![quinolinone with CH3, CH2CH3 on N, CF3/HO/CF3, CH3] |
| 38. ![quinolinone with CH2CH3, H-N, CF3/HO/CF3, CH3] | ![quinolinone with CH3CH2, CH3 on N, CF3/HO/CF3, CH3] |

-continued

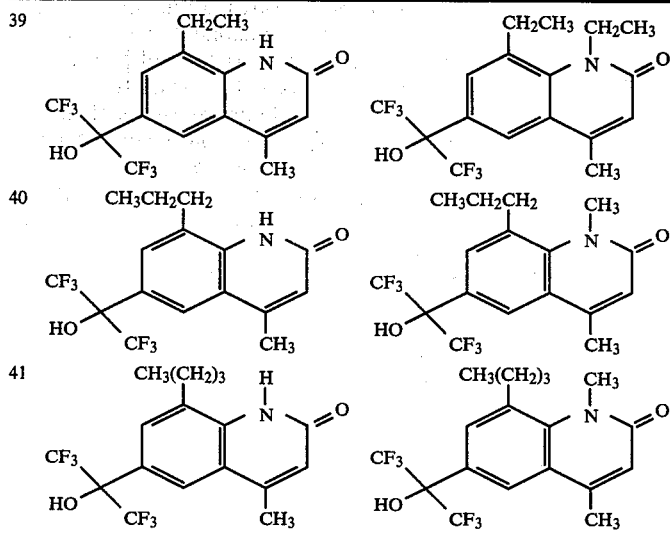

Example 42

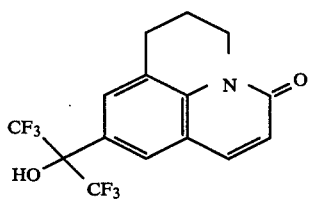

To a stirred solution of 15.0 g. (0.05 mole) of α,α-bis(-trifluoromethyl)-1,2,3,4-tetrahydro-6-quinoline- methanol in 50 ml. of anhydrous toluene at reflux is added dropwise 7.1 g. (0.05 mole) of malonyl dichloride. Reflux is continued until evolution of hydrogen chloride is complete. The toluene is then removed by evaporation, and the residue is refluxed with 120 ml. of phosphorus oxychloride for two hours. The solution is poured into ice water with stirring. When the excess phosphorus oxychloride is decomposed, the remaining tarry, insoluble material is filtered off, washed, and dried. The tarry material is chromatographed on silica gel with a mixture of toluene and ethyl acetate (60:40) to give a solid, which is recrystallized from a minimum of alcohol to give 7-chloro-2,3-dihydro-9-[2,2,2,-trifluoro-1-hydroxy-1-(trifluoromethyl)ethyl]-1H,5H-benzo[ij]quinolinzin-5-one, m.p. 238°–284°.

A mixture of 0.7 g. of 7-chloro-2,3-dihydro-9-[2,2,2-trifluoro-1-hydroxy-1-(trifluoromethyl)ethyl]-1H,5H-benzo[ij]quinolizin-5-one, 150 ml. of glacial acetic acid, 5 g. of sodium acetate trihydrate, and 0.5 g. of 10% palladium on charcoal is hydrogenated in a Parr shaker apparatus for 4 hours at an initial pressure of 3 atm. The catalyst is removed by filtration, solvent is removed by evaporation, and the residue is triturated with water. The insoluble material is filtered off, dried and recrystallized to give 2,3-dihydro-9-[2,2,2-trifluoro-1-hydroxy-1-(trifluoromethyl)ethyl]-1H,5H-benzo[ij]-quinolizin-5-one, m.p. 295°–296°.

EXAMPLE 43

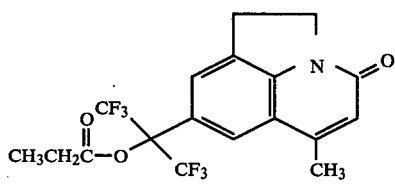

A stirred suspension of 3.5 g. (0.01 mole) of 1,2-dihydro-8-[2,2,2-trifluoro-1-hydroxy-1-(trifluoromethyl)-ethyl]-6-methyl-4H-pyrrolo[3,2,1-ij]quinolin-4-one and 50 ml. of propionic anhydride is refluxed for four hours. Then 50 ml. of water is added cautiously to the refluxing mixture. The mixture is stirred with a mixture of 200 ml. of ether and a solution of 50 g. of patassium bicarbonate in 300 ml. of water. The ether layer is separated, washed with saturated sodium chloride solution, dried with magnesium sulfate, and evaporated. The residue is recrystallized to give 2.45 g. (60%) of 1,2-dihydro-8-[2,2,2-trifluoro-1-hydroxy-1-(tri-fluoromethyl)ethyl]-6-methyl-4H-pyrrolo[3,2,1-ij]quinolin-4-one propanoate, m.p. 136°–137°.

EXAMPLE 44

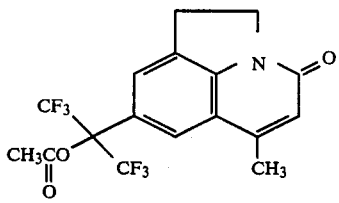

Substituting acetic anhydride for the propionic anhydride in Example 43 gives 1,2-dihydro-8-[2,2,2-trifluoro1-hydroxy-1-(trifluoromethyl)ethyl]-6-methyl-4H-pyrrolo[3,2,1-ij]quinolin-4-one acetate, m.p. 221.5°–223°.

EXAMPLE 45

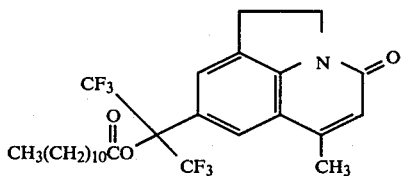

A stirred mixture of 3.5 g (0.01 mole) of 1,2-dihydro-8-[2,2,2-trifluoro-1-hydroxy-1-(trifluoromethyl)-ethyl]-6-methyl-4H-pyrrolo[2,3,1-ij]quinolin-4-one, 4 ml. of anhydrous pyridine, and 2.8 g. (0.012 mole) of lauroyl chloride is heated at reflux until homogeneous. The mixture is cooled and poured into excess 2N HCl. The mixture is extracted with ether. The ether extract is washed with cold 2N NaOH and then with saturated sodium chloride solution; it is then dried (MgSO$_4$) and evaporated. Recrystallization from methylcyclohexane gives waxy crystals of 1,2-dihydro-8-[2,2,2-trifluoro-1-hydroxy-1-(trifluoromethyl)ethyl]-6-methyl-4H-pyrrolo[3,2,1-ij]quinolin-4-one laurate, m.p. 72°–73°.

Anal. for $C_{24}H_{33}F_6NO_3$:
Calc'd.: C, 60.78; H, 6.23; N, 2.63
Found: C, 61.00; H, 6.37; N, 2.76

EXAMPLES 46–49

Following the procedure of Example 45 and using the appropriate chloride in place of lauroyl chloride, one can make the following products:

| Example No. | Acid Chloride | Product |
|---|---|---|
| 46 | benzoyl chloride | 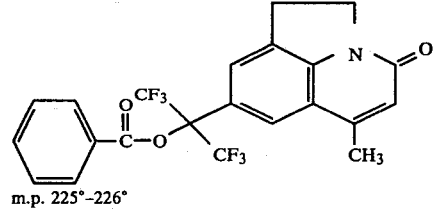 m.p. 225°–226° |
| 47 | crotonyl chloride | 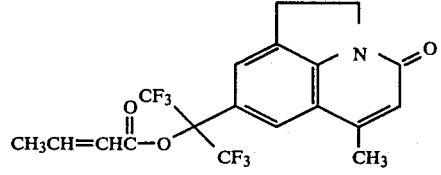 |
| 48 | isovaleryl chloride | 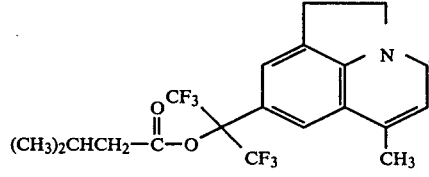 |
| 49 | phenylacetyl chloride | 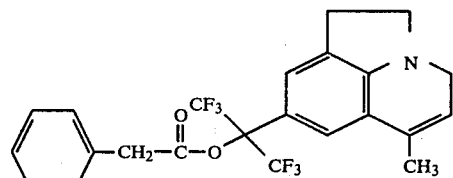 |

Example 50

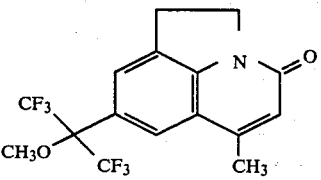

To a stirred mixture of 3.5 g of 1,2-dihydro-8-[2,2,2-trifluoro-1-hydroxy-1-(trifluoromethyl)ethyl]-6-methyl-4H-pyrrolo[3,2,1-ij]quinolin-4-one and 20 ml of dry dimethylformamide is added 1.3 g (0.012 mole) of potassium tert-butoxide in a dry nitrogen atmosphere. The mixture is heated gently to 100° and is allowed to cool. Then 1 ml (1.35 g, 0.011 mole) of dimethyl sulfate is added, and the mixture is warmed gently to 100°. The mixture is allowed to cool to room temperature and is poured into 100–200 ml of water. The precipitate is filtered off and then is triturated with 10% sodium hydroxide solution. The insoluble material is filtered off, washed with water, and dried. Recrystallization from alcohol gives 1.8 g (49%) of 1,2-dihydro-8-[2,2,2-trifluoro-1-methoxy-1-(trifluoromethyl)-ethyl]-6-methyl-4H-pyrrolo[3,2,1-ij]quinolin-4-one, m.p. 242°–243°.

EXAMPLE 51

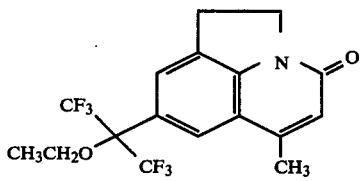

By using diethyl sulfate in place of the dimethyl sulfate in Example 50 one obtains 1,2-dihydro-8-[2,2,2-trifluoro-1-ethoxy-1-(trifluoromethyl(ethyl]-6-methyl-4H-pyrrolo[3,2,1-ij]quinolin-4-one, m.p. 189°–190°.

EXAMPLE 51a

By using benzyl chloride in place of dimethyl sulfate in Example 50 one obtains 1,2-dihydro-8-[2,2,2-trifluoro-1-benzyloxy-1-(trifluoromethyl)ethyl]-6-methyl-4H-pyrrolo[3,2,1-ij]quinolin-4-one, m.p. 207°–208°.

EXAMPLE 52

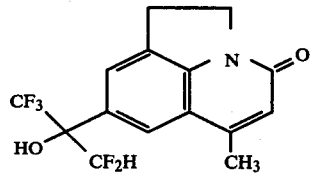

By the method of Example 7, α-(difluoromethyl)-α-(trifluoromethyl)-2,3-dihydro-1H-indole-5-methanol is converted to α-(difluoromethyl)-α-(trifluoromethyl)-1-(1,3-dioxobutyl)-2,3-dihydro-1H-indole-5-methanol, m.p. 140°–143°, which is cyclized by heating in sulfuric acid to give 1,2-dihydro-8-[2,2,-difluoro-1-hydroxy-1-(trifluoromethyl)ethyl]-6-methyl-4H-pyrrolo[3,2,1-ij]quinolin-4-one, m.p. 317°–318°.

EXAMPLE 53

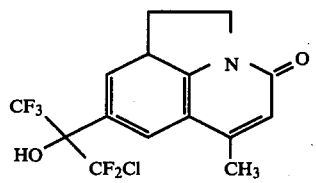

By the method of Example 7, α-(chlorodifluoromethyl)-α-(trifluoromethyl)-2,3-dihydro-1H-indole-5-methanol is converted to α-(chlorodifluoromethyl)-α-(trifluoromethyl)-1-(1,3-dioxobutyl)-2,3-dihydro-1H-indole-5-methanol, m.p. 160°–164°, which is cyclized by heating in sulfuric acid to give 1,2-dihydro-8 [2-chloro-2,2-difluoro-1-hydroxy-1-(trifluoromethyl)ethyl]-6-methyl-4H-pyrrolo[3,-2,1-ij]quinolin-4-one, m.p. 294°–295°.

EXAMPLE 54

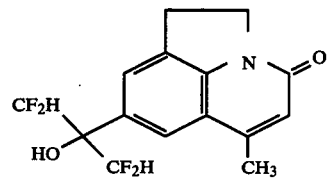

By the method of Example 7, α,α-bis(difluoromethyl)-2,3-dihydro-1H-indole-5-methanol is converted to α,α-bis(difluoromethyl)-1-(1,3-dioxobutyl)-2,3-dihydro-1H-indole-5-methanol, m.p. 148°–150°, which is cyclized by heating in sulfuric acid to give 1,2-dihydro-8-[2,2-difluoro1-hydroxy-1-(difluoromethyl)ethyl]-6-methyl-4H-pyrrolo[3,2,-1-quinolin-4-one, m.p. 310°–313°.

EXAMPLE 55

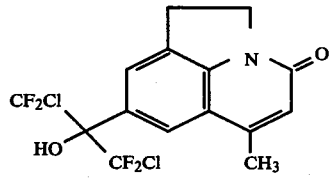

By the method of Example 7, αα-bis(chlorodifluoromethyl)2,3-dihydro-1H-indole-5-methanol is converted to α,α-bis(chlorodifluoromethyl)-1-(1,3-dioxobutyl)-2,3-dihydro-1H-indole-5-methanol, which is cyclized by heating in sulfuric acid to give 1,2-dihydro-8-[2-chloro-2,2-difluoro-1-hydroxy-1-(chlorodifluoromethyl)ethyl]-6-methyl-4H-pyrrolo[3,2,1-ij]quinolin-4-one, m.p. 256°–257°.

EXAMPLE 56

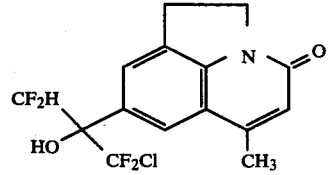

By the method of Example 7, α-(chlorodifluoromethyl)-α-(difluoromethyl)2,3-dihydro-1H-indole-5-methanol is converted to α-(chlorodifluoromethyl)-α-(difluoromethyl)-1-(1,3-dioxobutyl)-2,3-dihydro-1H-indole-5-methanol, m.p. 129.5°–134°, which is cyclized by heating in sulfuric acid to give 1,2-dihydro-8-[2-chloro-2,2-difluoro-1-hydroxy-1-(difluoromethyl)-ethyl]-6-methyl-4H-pyrrolo-[3,2,i-ij]quinolin-4-one, m.p. 264°–265°.

Dosage Forms

The antihypertensive agents of this invention can be administered to treat hypertension by any means that produces contact of the active agent with the agent's site of action in the body of a mammal. They can be administered by any conventional means available for use in conjunction with pharmaceuticals; either as individual therapeutic agents or in a combination of therapeutic agents. They can be administered, alone, but are generally administered with a pharmaceutical carrier selected on the basis of the chosen route of administration and standard pharmaceutical practice.

The dosage administered will, of course, vary depending upon known factors such as the pharmacodynamic characteristics of the particular agent, and its mode and route of administration; age, health, and weight of the recipient; nature and extent of symptoms, kind of concurrent treatment, frequency of treatment, and the effect desired. Usually a daily dosage of active ingredient can be about 0.01 to 50 milligrams per kilogram of body weight. Ordinarily 0.05 to 40, and preferably 0.2 to 20, milligrams per kilogram per day given in divided doses 2 to 4 time a day or in sustained release form is effective to obtain desired results. For the more potent compounds the daily dosage ranges are 0.01 to 10 milligrams per kilogram, preferably 0.05 to 10 milligrams per kilogram, and more preferably 0.05 to 5 milligrams per kilogram.

Dosage forms (compositions) suitable for internal administration contain from about 1.0 milligrams to about 100 milligrams of active ingredient per unit. In these pharmaceutical compositions the active ingredient will ordinarily be present in an amount of about 0.5–95% by weight based on the total weight of the composition.

The active ingredient can be administered orally in solid dosage forms, such as capsules, tablets, and powders, or in liquid dosage forms, such as elixirs, syrups, and suspensions; it can also be administered parenterally, in sterile liquid dosage forms.

Gelatin capsules contain the active ingredient and powdered carriers, such as lactose, sucrose, mannitol, starch, cellulose derivatives, magnesium stearate, stearic acid, and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric coated for selective disintegration in the gastrointestinal tract.

Liquid dosage forms for oral administration can contain coloring and flavoring to increase patient acceptance.

Suitable pharmaceutical carriers are described in *Remington's Pharmaceutical Sciences*, E. W. Martin, a standard reference text in this field.

Useful pharmaceutical dosage-forms for administration of the compounds of this invention can be illustrated as follows:

CAPSULES

A large number of unit capsules are prepared by filling standard two-piece hard gelatin capsules each with 5 milligrams of powdered active ingredient, 150 milligrams of lactose, 32 milligrams of talc, and 8 milligrams magnesium stearate.

CAPSULES

A mixture of active ingredient in soybean oil is prepared and injected by means of a positive displacement pump into gelatin to form soft gelatin capsules containing 2 milligrams of the active ingredient. The capsules are washed in petroleum ether and dried.

TABLETS

A large number of tablets are prepared by conventional procedures so that the dosage unit is 15 milligrams of active ingredient, 7 milligrams of ethyl cellulose, 0.2 milligrams of colloidal silicon dioxide, 7 milligrams of magnesium stearate, 11 milligrams of microcrystalline cellulose, 11 milligrams of cornstarch and 98.8 milligrams of lactose. Appropriate coatings may be applied to increase palatability or delay absorption.

SUSPENSION

An aqueous suspension is prepared for oral administration so that each 5 milliliters contain 10 milligrams of finely divided active ingredient, 500 milligrams of acacia, 5 milligrams of sodium benzoate, 1.0 grams of sorbitol solution, U.S.P., 5 milligrams of sodium saccharin, and 0.025 milliliters of vanilla tincture.

UTILITY

The antihypertensive activity of the compounds of this series is detected with a procedure using DOCA hypertensive rats, which have been shown to be a good predictor of human efficacy.

Rats are made hypertensive by subcutaneous implantation of pellets of desoxycorticosterone acetate (DOCA) and by giving saline solution to drink essentially according to the method described by Sturtevant [Annals of Internal Medicine, 49, 1281 (1958)]. Graded dose levels of each compound are administered orally to groups of 8 hypertensive rats. The compound is prepared in an aqueous polyvinyl alcohol/acacia vehicle and administered at a volume to body weight ratio of 5.0 ml/kg. Sixteen hypertensive rats receiving the aqueous vehicle by the same route serve as controls for each test. At various intervals of time after treatment, usually 90 minutes, the systolic arterial blood pressure of each rat is determined by a modification of the microphone-manometer technique [Friedman, M. and Freed, S. C., Proc. Soc. Exp. Biol, and Med., 70, 670 (1949)]. That dose of compound which produces a 30 mm mercury (mm Hg) reduction in blood pressure when compared to the mean systolic arterial blood pressure of the control animals is then determined (Effective Dose 30).

When testing by this procedure, the following $ED_{30}$ dosages were determined.

ANTIHYPERTENSIVE CARBOSTYRILS

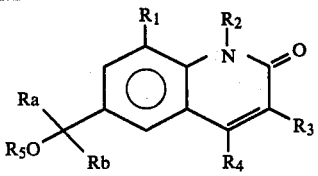

| COMPOUND | | | | | | | |
|---|---|---|---|---|---|---|---|
| R₁ | R₂ | R₃ | R₄ | R₅ | Ra | Rb | ED₅₀ mg/kg |
| —CH₂—CH₂—CH₂— | | H | CH₃ | H | CF₃ | CF₃ | 1.0 |
| —CH₂—CH₂—CH— | CH₃ | H | CH₃ | H | CF₃ | CF₃ | 0.66 |
| —CH—CH₂—CH₂— | CH₃ | H | CH₃ | H | CF₃ | CF₃ | 3.6 |
| —CH₂—CH₂—CH₂— | | H | —CH₂CH₃ | H | CF₃ | CF₃ | 0.27 |
| —CH₂—CH₂—CH₂— | | Cl | CH₃ | H | CF₃ | CF₃ | 1.6 |
| —CH₂—CH₂—CH₂— | | Br | CH₃ | H | CF₃ | CF₃ | 9.0 |
| —CH₂—CH₂— | | NO₂ | CH₃ | H | CF₃ | CF₃ | 1.5 |
| —CH₂—CH₂— | | NH₂ | CH₃ | H | CF₃ | CF₃ | 5.4 |
| —CH₂—CH₂— | | H | CH₃ | H | CF₃ | CF₃ | 0.13 |
| —CH₂—CH— | CH₃ | H | CH₃ | H | CF₃ | CF₃ | 0.047 |
| —CH—CH₂— | CH₃ | H | CH₃ | H | CF₃ | CF₃ | 0.60 |
| —CH₂—CH₂— | | H | —CH₂CH₃ | H | CF₃ | CF₃ | 0.11 |
| —CH₂—CH₂—CH₂—CH₂ | | H | CH₃ | H | CF₃ | CF₃ | 1.3 |
| CH₃ | H | H | CH₃ | H | CF₃ | CF₃ | 3.7 |
| C₂H₅ | H | H | CH₃ | H | CF₃ | CF₃ | 1.3 |
| H | H | H | CH₃ | H | CF₃ | CF₃ | 4.1 |
| H | CH₃ | H | CH₃ | H | CF₃ | CF₃ | 0.4 |
| H | —CH₂CH₃ | H | CH₃ | H | CF₃ | CF₃ | 1.2 |
| H | —(CH₂)₃CH₃ | H | CH₃ | H | CF₃ | CF₃ | 5.2 |
| —CH₂—CH₂—CH₂— | | H | H | H | CF₃ | CF₃ | ~ 3-9 |
| —CH₂—CH₂— | | H | CH₃ | propionate | CF₃ | CF₃ | 0.22 |
| —CH₂—CH₂— | | H | CH₃ | acetate | CF₃ | CF₃ | 0.20 |
| —CH₂—CH₂— | | H | CH₃ | laurate | CF₃ | CF₃ | 0.12 |
| —CH₂—CH₂— | | H | CH₃ | benzoate | CF₃ | CF₃ | 0.25 |
| —CH₂—CH₂— | | H | CH₃ | CH₃ | CF₃ | CF₃ | 0.35 |
| —CH₂—CH₂— | | H | CH₃ | CH₃CH₂— | CF₃ | CF₃ | 0.50 |
| —CH₂—CH₂— | | H | CH₃ | H | CF₃ | CF₂H | 0.075 |
| —CH₂—CH₂— | | H | CH₃ | H | CF₃ | CF₂Cl | 0.07 |
| —CH₂—CH₂— | | H | CH₃ | H | CF₂H | CF₂H | 1.2 |

In the above examples, all parts are by weight and temperatures are in degrees centigrade unless otherwise indicated.

What is claimed is:

1. A compound of the formula:

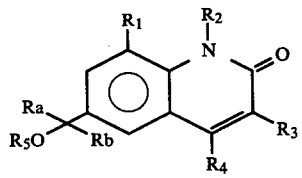

where
$R_1$ = H or alkyl of 1-4 carbons;
$R_2$ = H or alkyl of 1-4 carbons;
provided when $R_1$ = alkyl, $R_2$ = H, —CH₃ or —CH₂CH₃; or
$R_1 + R_2$ taken together, is

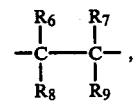

(a)

where
$R_6$ = H or —CH₃;
$R_7$ = H or —CH₃;
$R_8$ = H or alkyl of 1-4 carbons;
$R_9$ = H or alkyl of 1-4 carbons; or
$R_8 + R_9$, taken together, is —(CH₂)₄—;
provided
  (i) at least one of $R_6$, $R_7$, $R_8$, or $R_9$ = H; and
  (ii) the sum of the carbons of $R_6$, $R_7$, $R_8$, and $R_9$ is not more than 6;

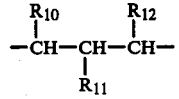

(b)

where
$R_{10}$ = H, —CH₃, or —CH₂CH₃;
$R_{11}$ = H, —CH₃, or —CH₂CH₃;

$R_{12}=H$, $-CH_3$, or $-CH_2CH_3$; or
$R_{11}$, taken together with $R_{10}$ or $R_{12}$, is $-(CH_2)_4-$;
provided at least one of $R_{10}$, $R_{11}$, or $R_{12}=H$; or (c) $-(CH_2)_4-$;

$R_3=H$, $CH_3$, F, Cl, Br, $NO_2$, $NH_2$, or OH;

$R_4=H$ or alkyl of 1-4 carbons;

$R_5=H$, benzyl, alkanoyl, alkenoyl, and hydrocarbon aroyl or alkyl of 1-6 carbons;

$Ra=CF_3$, $CF_2Cl$ or $CF_2H$;

$Rb=CF_3$, $CF_2Cl$ or $CF_2H$;

and when $R_5=H$, its pharmaceutical suitable metal salt.

2. The compound of claim 1 where $R_3$ is hydrogen.

3. The compound of claim 1 where $R_4$ is methyl or ethyl.

4. The compound of claim 1 where $R_5$ is hydrogen.

5. The compound of claim 1 where $R_1$ and $R_2$, taken together, are:

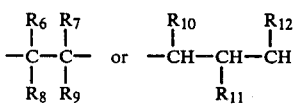

6. The compound of claim 5 where $R_1$ and $R_2$, taken together, are:

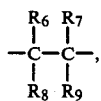

and $R_6$, $R_7$, and $R_8$ are hydrogen.

7. The compound of claim 5 where $R_1$ and $R_2$, taken together, are:

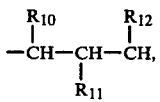

and $R_{10}$ and $R_{11}$ are hydrogen.

8. The compound of claim 6 where $R_3$ is hydrogen and $R_4$ is methyl or ethyl.

9. The compound of claim 7 where $R_3$ is hydrogen and $R_4$ is methyl or ethyl.

10. The compound of claim 8 where $R_5$ is hydrogen.

11. The compound of claim 9 where $R_5$ is hydrogen.

12. The compound of claim 8 where Ra is $CF_3$ and Rb is $CF_3$, $CF_2Cl$ or $CF_2H$.

13. The compound of claim 9 where Ra is $CF_3$ and Rb is $CF_3$, $CF_2Cl$ or $CF_2Cl$.

14. The compound of claim 1 where Ra and Rb both are $CF_3$.

15. The compound of claim 1:
2,3-dihydro-9-[2,2,2-trifluoro-1-hydroxy-1-(trifluoromethyl)ethyl]-7-methyl-1H,5H-benzo[ij]quinolizin-5-one.

16. The compound of claim 1:
2,3-dihydro-3,7-dimethyl-9-[2,2,2-trifluoro-1-hydroxy-1-(trifluoromethyl)ethyl]-1H,5H-benzo[ij]quinolizin-5-one.

17. The compound of claim 1:
2,3-dihydro-7ethyl-9-[2,2,2-trifluoro-1-hydroxy-1-(trifluoromethyl)ethyl]-1H,5H-benzo[ij]quinolizin-5-one.

18. The compound of claim 1:
1,2-dihydro-8-[2,2,2-trifluoro-1-hydroxy-1-(trifluoromethyl)ethyl]-6-methyl-4H-pyrrolo[3,2,1-ij]quinolin-4-one.

19. The compound of claim 1: 1,2-dihydro-2,6-dimethyl-8-[2,2,2-trifluoro-1-hydroxy-1-(trifluoromethyl)ethyl]-4H-pyrrolo[3,2,1-ij]quinolin-4-one.

20. The compound of claim 1:
1,2-dihydro-6-ethyl-8-[2,2,2-trifluoro-1-hydroxy-1-(trifluoromethyl)ethyl]-4H-pyrrolo[3,2,1-ij]quinolin-4-one.

21. The compound of claim 1:
1,2-dihydro-8-[2,2-difluoro-1-hydroxy-1-(trifluoromethyl)ethyl]-6-methyl-4H-pyrrolo[3,2,1-ij]quinolin-4-one.

22. The compound of claim 1:
1,2-dihydro-8-[2-chloro-2,2-difluoro-1-hydroxy-1-(trifluoromethyl)ethyl]-6-methyl-4H-pyrrolo[3,2,1-ij]quinolin-4-one.

23. The compound of claim 1:
1,2-dihydro-8-[2,2-difluoro-1-hydroxy-1-(difluoromethyl)ethyl]-6-methyl-4H-pyrrolo[3,2,1-ij]quinolin-4-one.

24. A pharmaceutical composition comprising a pharmaceutically suitable carrier and an effective antihypertensive amount of a compound of claim 1.

25. A pharmaceutical composition comprising a pharmaceutically suitable carrier and an effective antihypertensive amount of a compound of claim 2.

26. A pharmaceutical composition comprising a pharmaceutically suitable carrier and an effective antihypertensive amount of a compound of claim 3.

27. A pharmaceutical composition comprising a pharmaceutically suitable carrier and an effective antihypertensive amount of a compound of claim 4.

28. A pharmaceutical composition comprising a pharmaceutically suitable carrier and an effective antihypertensive amount of a compound of claim 5.

29. A pharmaceutical composition comprising a pharmaceutically suitable carrier and an effective antihypertensive amount of a compound of claim 6.

30. A pharmaceutical composition comprising a pharmaceutically suitable carrier and an effective antihypertensive amount of a compound of claim 7.

31. A pharmaceutical composition comprising a pharmaceutically suitable carrier and an effective antihypertensive amount of a compound of claim 8.

32. A pharmaceutical composition comprising a pharmaceutically suitable carrier and an effective antihypertensive amount of a compound of claim 9.

33. A pharmaceutical composition comprising a pharmaceutically suitable carrier and an effective antihypertensive amount of a compound of claim 10.

34. A pharmaceutical composition comprising a pharmaceutically suitable carrier and an effective antihypertensive amount of a compound of claim 11.

35. A pharmaceutical composition comprising a pharmaceutically suitable carrier and an effective antihypertensive amount of a compound of claim 12.

36. A pharmaceutical composition comprising a pharmaceutically suitable carrier and an effective antihypertensive amount of a compound of claim 13.

37. A pharmaceutical composition comprising a pharmaceutically suitable carrier of an effective antihypertensive amount of a compound of claim 14.

38. A pharmaceutical composition comprising a pharmaceutically suitable carrier of an effective antihypertensive amount of the compound of claim 15.

39. A pharmaceutical composition comprising a pharmaceutically suitable carrier of an effective antihypertensive amount of the compound of claim 16.

40. A pharmaceutical composition comprising a pharmaceutically suitable carrier of an effective antihypertensive amount of the compound of claim 17.

41. A pharmaceutical composition comprising a pharmaceutically suitable carrier of an effective antihypertensive amount of the compound of claim 18.

42. A pharmaceutical composition comprising a pharmaceutically suitable carrier of an effective antihypertensive amount of the compound of claim 19.

43. A pharmaceutical composition comprising a pharmaceutically suitable carrier of an effective antihypertensive amount of the compound of claim 20.

44. A pharmaceutical composition comprising a pharmaceutically suitable carrier of an effective antihypertensive amount of the compound of claim 21.

45. A pharmaceutical composition comprising a pharmaceutically suitable carrier of an effective antihypertensive amount of the compound of claim 22.

46. A pharmaceutical composition comprising a pharmaceutically suitable carrier of an effective antihypertensive amount of the compound of claim 23.

47. A method of treating hypertension in a mammal which comprises administering to the mammal an effective antihypertensive amount of a compound of claim 1.

48. A method of treating hypertension in a mammal which comprises administering to the mammal an effective antihypertensive amount of a compound of claim 2.

49. A method of treating hypertension in a mammal which comprises administering to the mammal an effective antihypertensive amount of a compound of claim 3.

50. A method of treating hypertension in a mammal which comprises administering to the mammal an effective antihypertensive amount of a compound of claim 4.

51. A method of treating hypertension in a mammal which comprises administering to the mammal an effective antihypertensive amount of a compound of claim 5.

52. A method of treating hypertension in a mammal which comprises administering to the mammal an effective antihypertensive amount of a compound of claim 6.

53. A method of treating hypertension in a mammal which comprises administering to the mammal an effective antihypertensive amount of a compound of claim 7.

54. A method of treating hypertension in a mammal which comprises administering to the mammal an effective antihypertensive amount of a compound of claim 8.

55. A method of treating hypertension in a mammal which comprises administering to the mammal an effective antihypertensive amount of a compound of claim 9.

56. A method of treating hypertension in a mammal which comprises administering to the mammal an effective antihypertensive amount of a compound of claim 10.

57. A method of treating hypertension in a mammal which comprises administering to the mammal an effective antihypertensive amount of a compound of claim 11.

58. A method of treating hypertension in a mammel which comprises administering to the mammal an effective antihypertensive amount of a compound of claim 12.

59. A method of treating hypertension in a mammal which comprises administering to the mammal an effective antihypertensive amount of a compound of claim 13.

60. A method of treating hypertension in a mammal which comprises administering to the mammal an effective antihypertensive amount of a compound of claim 14.

61. A method of treating hypertension in a mammal which comprises administering to the mammal an effective antihypertensive amount of the compound of claim 15.

62. A method of treating hypertension in a mammal which comprises administering to the mammal an effective antihypertensive amount of the compound of claim 16.

63. A method of treating hypertension in a mammal which comprises administering to the mammal an effective antihypertensive amount of the compound of claim 17.

64. A method of treating hypertension in a mammal which comprises administering to the mammal an effective antihypertensive amount of the compound of claim 18.

65. A method of treating hypertension in a mammal which comprises administering to the mammal an effective antihypertensive amount of the compound of claim 19.

66. A method of treating hypertension in a mammal which comprises administering to the mammal an effective antihypertensive amount of the compound of claim 20.

67. A method of treating hypertension in a mammal which comprises administering to the mammal an effective antihypertensive amount of the compound of claim 21.

68. A method of treating hypertension in a mammal which comprises administering to the mammal an effective antihypertensive amount of the compound of claim 22.

69. A method of treating hypertension in a mammal which comprises administering to the mammal an effective antihypertensive amount of the compound of claim 23.

* * * * *